United States Patent
Scifert

(10) Patent No.: US 7,897,164 B2
(45) Date of Patent: Mar. 1, 2011

(54) COMPOSITIONS AND METHODS FOR NUCLEUS PULPOSUS REGENERATION

(75) Inventor: Jeffrey L. Scifert, Arlington, TN (US)

(73) Assignee: Warsaw Orthopedic, Inc

( * ) Notice: Subject to any disclaimer, the term of this patent is extended or adjusted under 35 U.S.C. 154(b) by 55 days.

(21) Appl. No.: 12/261,329

(22) Filed: Oct. 30, 2008

(65) Prior Publication Data

US 2010/0112029 A1 May 6, 2010

(51) Int. Cl.
*A61K 38/16* (2006.01)
*A61K 38/17* (2006.01)
*A61K 38/18* (2006.01)
*A61K 38/19* (2006.01)
*A61K 38/30* (2006.01)

(52) U.S. Cl. ............ 424/422; 424/425; 424/426; 514/1.1; 514/16.7; 514/20.9; 514/21.2; 514/7.6; 514/8.2; 514/8.5; 514/8.8; 514/8.9

(58) Field of Classification Search .......... None
See application file for complete search history.

(56) References Cited

U.S. PATENT DOCUMENTS

| | | | |
|---|---|---|---|
| 6,312,725 B1 | 11/2001 | Wallace et al. | |
| 6,479,065 B2 | 11/2002 | Jaworowicz et al. | |
| 6,703,041 B2 | 3/2004 | Burns et al. | |
| 6,958,078 B2 * | 10/2005 | Goel et al. | 623/17.16 |
| 6,998,074 B1 | 2/2006 | Radulescu | |
| 7,135,140 B2 | 11/2006 | Shinohara et al. | |
| 7,332,351 B2 | 2/2008 | Tan et al. | |
| 7,381,716 B2 | 6/2008 | Sung et al. | |
| 2007/0093912 A1 * | 4/2007 | Borden | 623/23.75 |
| 2008/0065228 A1 * | 3/2008 | Kim | 623/23.61 |

FOREIGN PATENT DOCUMENTS

WO    WO 2006/002365 A2 *    1/2006

* cited by examiner

*Primary Examiner*—Elizabeth C. Kemmerer

(57) ABSTRACT

Compositions for nucleus pulposus regeneration is provided. Such composition may comprise a scaffolding material and a pore creating agent dispersed within the scaffolding material. The pore creating agent is removed from the scaffolding material in vivo, after the composition is administered to a patient. The pore creating agent may include an active agent, such as a growth factor, which may be released as the pore creating agent is being gradually removed from the scaffolding material. In addition, removal of the pore creating agent results in a porous scaffold for cells capable of regeneration of nucleus pulposus, either existing in situ or delivered separately, to attach to for further proliferation and regeneration.

19 Claims, 2 Drawing Sheets

COMPOSITIONS AND METHODS FOR NUCLEUS PULPOSUS REGENERATION

FIELD OF THE INVENTION

This invention relates to compositions and method for regeneration of nucleus pulposus.

BACKGROUND

Intervertebral discs function to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

Degenerated discs are a significant source of spine-related pain. As people age, the nucleus pulposus begins to dehydrate. Dehydrated disc have a very limited ability to absorb shock and are a significant source of spine-related pain. In addition, the annulus fibrosis may tear due to an injury or the aging process allowing the nucleus pulposus to extrude through the tear. This condition is known as disc herniation. It is very common for the herniated disc to press against spinal nerves located near the posterior side of each disc all along the spine, causing radiating pain, numbness, tingling, and diminished strength and/or range of motion. In addition, the contact of the inner nuclear gel, which contains inflammatory proteins, with a nerve can also cause significant pain.

Amongst sufferers of chronic pain, spine-related problems constitute the bulk of such complaints. Spinal pain has been estimated to exist in as much as 66% of the general population. Beyond the substantial discomfort that back pain inflicts upon individuals, spine-related pain also incurs heavy societal costs. For example, as many as one million spine surgeries, and as many as five million interventional procedures, are estimated to be performed in the United States each year. Well beyond the purely medical and psychological burdens imposed by such procedures, the subsequent social costs related to productivity, disability compensation and lost taxes are substantial.

Although procedures for treating intervertebral disc injuries are known, there is still a need in the art for improved compositions and methods for treatment of such injuries.

SUMMARY

In one aspect, compositions for nucleus pulposus regeneration are provided. Such compositions may comprise a scaffolding material and a pore creating agent dispersed within the scaffolding material. In some embodiments, such compositions may be administered in combination with cells capable of regeneration of nucleus pulposus.

The scaffolding material may be selected from a resorbable or a non-resorbable material having a low viscosity for easy administration of the composition to patients. The pore creating agent is gradually removed from the scaffolding material in vivo creating a porous scaffold for the nucleus pulposus cells, either existing in situ or delivered separately, to attach to for further proliferation and regeneration. In the embodiments employing resorbable scaffolding material, the rate of removal of the pore creating material from the scaffolding is faster than the rate of resorbtion of the scaffolding material.

In some embodiments, the pore creating material may include one or more biologically active agents that may promote nucleus pulposus regeneration. Suitable biologically active agents include, but are not limited to, Vascular Endothelial Growth Factors (VEGFs), Connective Tissue Growth Factors (CTGFs), Platelet Derived Growth Factors (PDGFs), insulin-related growth factor-I (IGF-I), insulin-related growth factor-II (IGF-II); fibroblast growth factor (FGF), beta-2-microglobulin (BDGF II), Bone Morphogenetic Proteins (BMPs, e.g., BMP-2 and/or GDF-5), Transforming Growth Factor betas (TGF-βs) or combinations thereof. The one or more biologically active agents may be released from the pore creating agent as the pore creating agent is being removed from the scaffolding material.

In another aspect, methods of nucleus pulposus regeneration are provided. Such methods may comprise administering to a patient a therapeutically effective amount of a composition described above.

DETAILED DESCRIPTION

Figure 1:
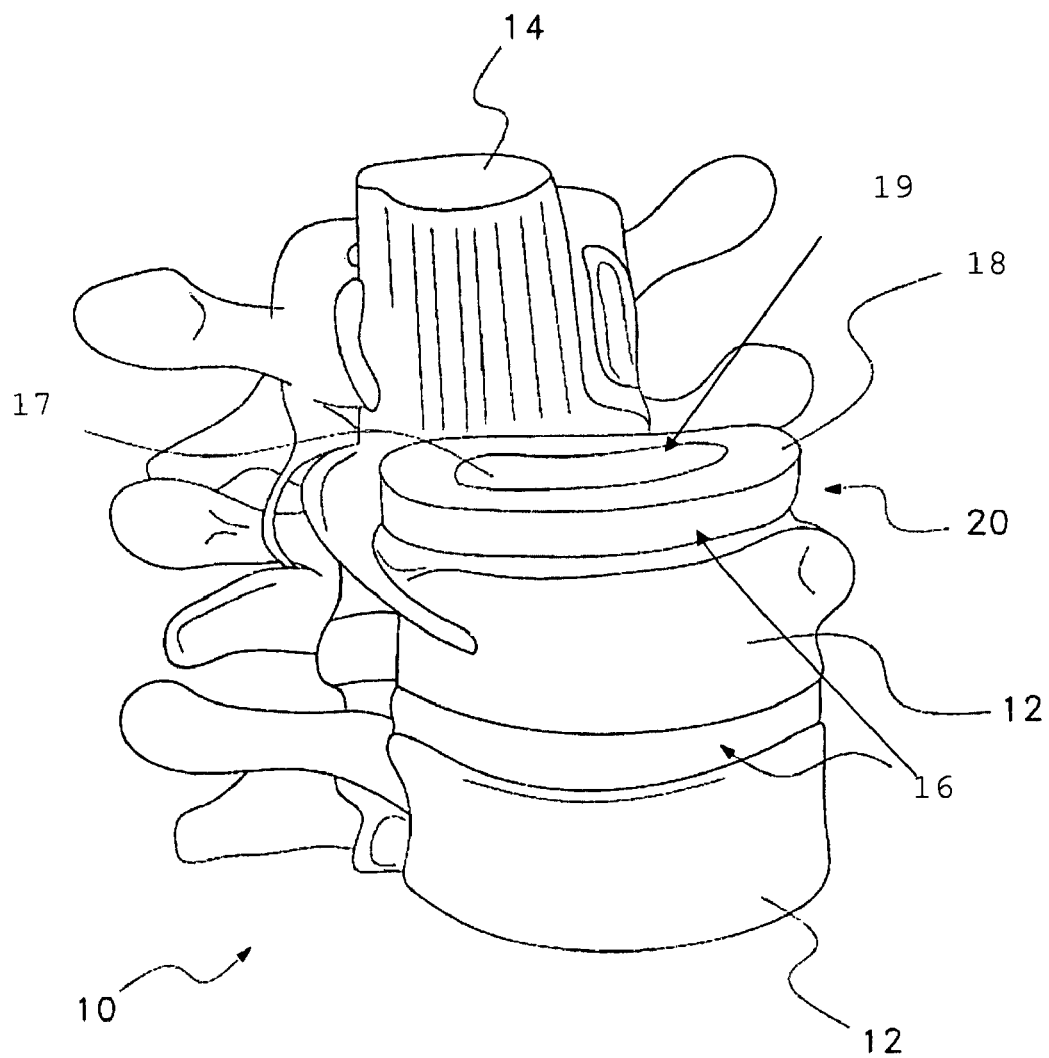
FIG. 1 is a cross-sectional view of an intervertebral disc.

As shown in FIG. 1, the spine 10 is composed of a column of vertebrae 12 that are individually separated from each other by intervertebral discs 16. The spinal cord 14 runs through the length of the spine 10. The discs 16 are an important part of the entire spinal column 10, and act like shock absorbers and stabilizers between adjacent vertebrae 12. The discs 16 must be able to absorb mechanical loads while simultaneously permitting constrained flexing of the spine 10.

Each disc 16 comprises a strong, fibrous outer region 18 that defines a disc space 19, which holds a relatively soft inner region 17. The soft inner region 17 is called the nucleus pulposus, and the reinforcing outer region 18 is called the annulus fibrosis. The nucleus pulposus 17 distributes mechanical loads placed upon the disc 16, while the annulus fibrosis 18 provides structural integrity and constrains the nucleus pulposus 17 to a specific spinal region.

Figure 2:
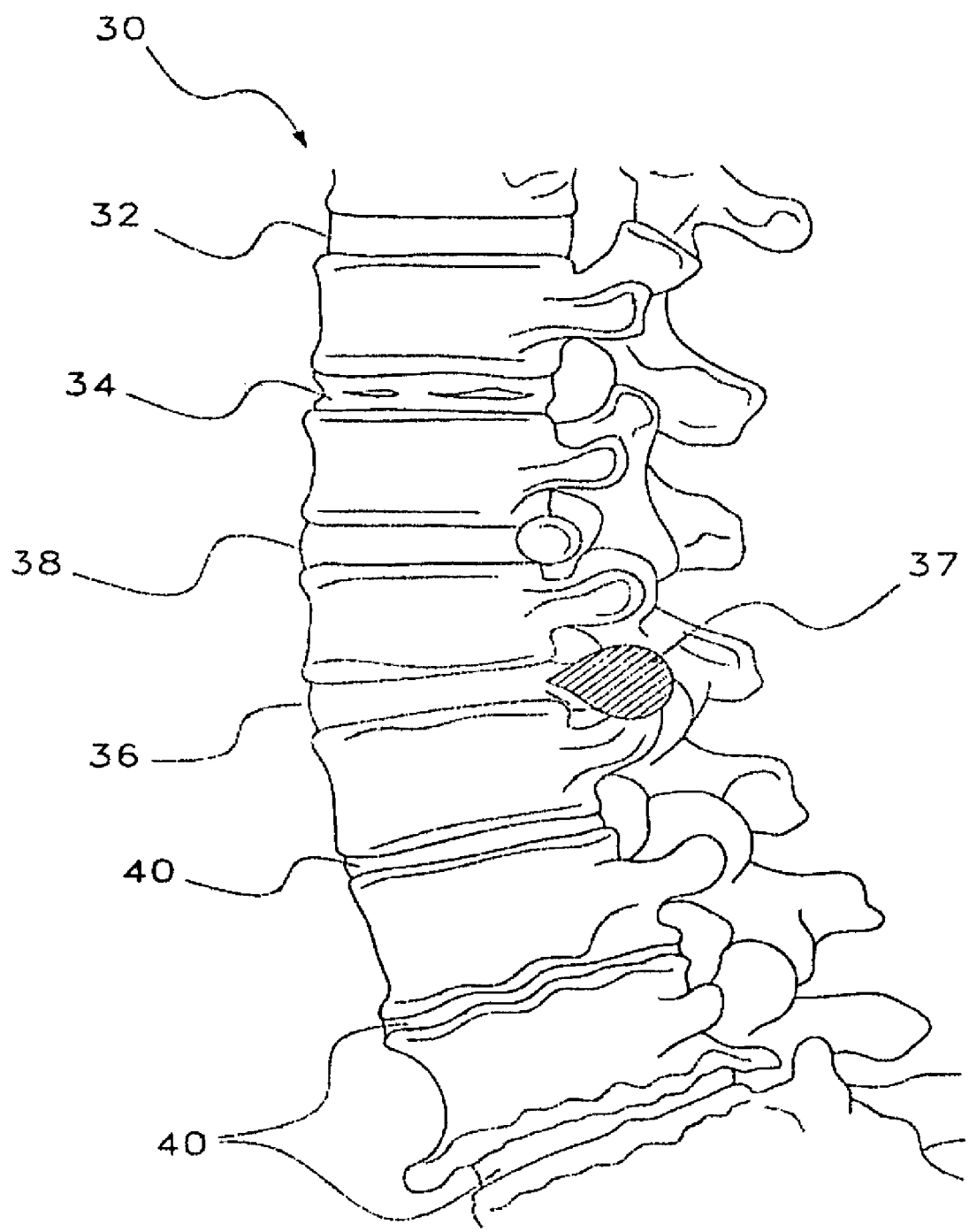
FIG. 2 illustrates a spinal column having multiple discs exhibiting different symptoms and degrees of degeneration.

As people age, the nucleus pulposus and annulus fibrosis may loose their ability to perform its functions due to disease or injury. FIG. 2 shows a spinal column 30 with discs exhibiting different symptoms and degrees of degeneration. For reference, a healthy disc 32 is also shown. Degeneration of a disc can include rupturing as shown by discs 34 and 36. Disc 34 exhibits rupturing by way of tears in the annulus fibrosus. Disc 36 shows signs of ruptured herniation, in which the nucleus pulposus material 37 has extruded past the annulus fibrosus and extends externally from the disc 36; the annulus fibrosus has ruptured, thus permitting release of the nucleus pulposus. Contained herniation is shown by disc 38. In disc 38, herniation of the nucleus pulposus material creates bulging of the annulus fibrosis; no nucleus pulposus material, however, escapes from the confines of the annulus fibrosis. Disc 38 is thus a non-ruptured, herniated disc; the annulus fibrosis of disc 38 does not exhibit tearing, rupturing or the like. Discs 40 shows signs of thinning, but otherwise no signs of rupturing as there are no tears in the annulus fibrosis of the discs 40, nor is there any leakage of nucleus pulposus material from the discs 40.

Compositions are provided for treating intervertebral disc injuries and degeneration by regeneration of nucleus pulposus tissue, including repairing, replacing and augmenting the native nucleus pulposus. Such composition may comprise a scaffolding material and a pore creating agent dispersed within the scaffolding material. The pore creating agent is removed from the scaffolding material in vivo, after the composition is administered to a patient. The pore creating agent may include an active agent, such as a growth factor, which may be released as the pore creating agent is being gradually removed from the scaffolding material. In addition, removal of the pore creating agent results in a porous scaffold for cells capable of regeneration of nucleus pulposus, either existing in situ or delivered separately, to attach to for further proliferation and regeneration.

The term "scaffolding material" means a resorabable or non-resorbable material having medium to low viscosity that, when injected into a disc space, provides a scaffold onto which nucleus pulposus cells may proliferate and regenerate. Because the scaffolding material will replace or augment the natural tissue until the nucleus pulposus is regenerated, the scaffolding material preferably possesses the same properties as the natural nucleus pulposus. For example, the materials are preferably selected so the formed implants have sufficient load bearing capacity. In preferred embodiments, a compressive strength of at least about 0.1 Mpa is desired, although compressive strengths in the range of about 1 Mpa to about 20 Mpa are more preferred. In addition, the material may preferably possess such qualities as mechanical strength, promotion of tissue formation, biodegradability, biocompatibility, sterilizability, minimal curing or setting time, optimum curing temperature, and medium to low viscosity for easy introduction into the disc space, and ability to withstand the large number of loading cycles experienced by the spine. In some embodiments, the scaffolding material may set up or partially set up upon delivery. Preparation of in-situ curable materials is known in the art and is disclosed, for example, in U.S. Pat. Nos. 6,703,041, 6,312,725, and 7,135,140.

In the embodiments employing resorbable scaffolding material, the scaffolding material may be resorbed over about 2 weeks to about 12 weeks, and more preferably over about 4 weeks to about 8 weeks, and most preferably over about 4 weeks to about 6 weeks.

A wide variety of biocompatible polymeric materials may be used as the scaffolding materials. Such materials include, but are not limited to, elastic materials, such as elastomeric materials, hydrogels or other hydrophilic polymers, or composites thereof. Suitable elastomers include silicon, polyurethane, copolymers of silicon and polyurethane, polyolefins, such as polyisobutylene and polyisoprene, neoprene, nitrile, vulcanized rubber and combinations thereof. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene. Suitable hydrogels include natural hydrogels, and those formed from polyvinyl alcohol, acrylamides such as polyacrylic acid and poly(acrylonitrile-acrylic acid), non-resorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof.

Other suitable examples of the scaffolding materials include biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and soldium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicon-based materials, polyethylene terephthalate, polycarbonate, thermoplastic elastomers and copolymers such as ether-ketone polymers such as poly(etheretherketone).

The term "pore creating agent" means a substance that is dispersed within the scaffolding material prior to delivery into the disc space and that creates a porous structure when removed from the scaffolding material. In instant compositions, the initial ratio of the scaffolding material to the pore creating agent is between about 5% and about 95%, more preferably between about 15% and about 85%, and most preferably between about 25% and about 75%.

In the context of this application, the pore creating agent is removed from the scaffolding material in vivo, after the composition is injected into a disc space. The term "removed" means gradual removal by resorbtion, resorption, dissolution, bursting, disintegration, degradation and so forth. The pore creating agent may be removed from the scaffolding material in between about 12 hours and about 96 hours, and more preferably between about 24 hours and about 72 hours, and most preferably between about 24 hours and about 48 hours. Removal of the pore creating agent from the scaffolding material, creates pores in the range of about 50 microns and about 400 microns, and more preferably in the range of about 100 microns and about 300 microns, and most preferably in the range of about 100 microns and about 200 microns and results in porosity of between about 60% and about 90%, and more preferably between about 75% and about 95%, and most preferably between about 80% and about 95%.

In some embodiments, the pore creating agent may comprise microparticles or nanoparticles, such as spheres, rods, pellets, beads, and so forth, made from resorbable materials. In preferred embodiments, the pore creating material is provided as microspheres with a diameter between about 50 microns to 400 microns, and more preferably between about 100 microns and about 300 microns, and most preferably between about 100 microns and about 200 microns.

Many of the bioresorbable materials suitable for use as scaffolding materials are also suitable for use as microparticles or nanoparticles. Again, if a resorbable material is used as a scaffolding material, the rate of removal of the pore creating material from the scaffolding material is faster than the rate of resorbtion of the scaffolding material by the patient's body. If desired, the pore creating agent and the scaffolding materials may be made from the same resorbable material, but the scaffolding material may be modified, such as by crosslinking, to ensure that its stays in the body for longer period of time. For example, the microparticles may be made of hydrogels, fast resorbing cements or ceramics, hyaluronic acid, collagen, sugars or polysaccharides, and so forth.

Microparticles or nanoparticles, with or without the biologically active agent, may be prepared by any techniques known and used in the art. Such techniques include, but are not limited to, single and double emulsion solvent evaporation, spray drying, solvent removal, phase separation, simple and complex coacervation, and interfacial polymerization. Suitable techniques for preparing microparticles or nanoparticles, with or without the biologically active agent are disclosed, for example, in Remington: The Science and Practice of Pharmacy, $21^{st}$ edition, Lippincott Williams & Wilkins (2005) and U.S. Pat. Nos. 6,479,065, 6,998,074, 7,381,716, and 7,332,351.

By way of non limiting example, microspheres may be produced by extrusion-spheroidization, where the active pharmaceutical ingredient and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In other embodiments, the pore creating agent may comprise a liposome. Generally, liposomes comprise an enclosed lipid droplet having a core, typically an aqueous core, containing a compound, such as a biologically active agent. The compound may be chemically conjugated to a lipid component of the liposome. Alternatively, the compound may be simply contained within the aqueous compartment inside the liposome. Liposomes are commercially available from a variety of suppliers or may be prepared according to known methods, such as the methods described, for example, in U.S. Pat. Nos. 6,855,296 and 6,984,397. In preferred embodiments, liposomes are shaped as microspheres with a diameter between about 50 microns to 400 microns, and more preferably between about 100 microns and about 300 microns, and most preferably between about 100 microns and about 200 microns.

In yet other embodiments, the pore creating agent may comprise microbubbles. Microbubbles may be formed in vitro and mixed with the scaffolding material or may be created in vivo. By way of non-limiting example, to prepare microbubbles in vitro, a vial containing a surfactant solution and gas in the headspace of the vial can be sonicated with a low power ultrasound. Once the sonication is accomplished, the microbubble solution can be withdrawn from the vial and mixed with the scaffolding material. Alternatively, the scaffolding material may be mixed with a liquid solution and an effervescent agent that is activated when the composition of the scaffolding material and pore creating agent is administered to a patient, producing microbubbles. The microbubbles may be produced together with a bioactive substance, thus potentially incorporating it into the microbubble's shell or lumen. Disintegration of the microbubbles creates pores in the scaffolding material and releases the biologically active agent, if one is included.

In some embodiments, the instant compositions may include a biologically active agent. For the purposes of the instant disclosure, the term "biologically active agent" means an agent that promotes, induces, increases, or accelerates nucleus pulposus regeneration. The term also includes agents that prevent formation of or that block substances responsible for nucleus pulposus regeneration. Suitable biologically active agents include, but are not limited to, Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Fibroblast Growth Factors (FGFs); Platelet Derived Growth Factors (PDGFs), including PDGF-A, PDGF-B, PDGF-C, PDGF-D, and GDF-5; rhGDF-5, insulin-related growth factor-I (IGF-I), insulin-related growth factor-II (IGF-II); fibroblast growth factor (FGF) and beta-2-microglobulin (BDGF II), Bone Morphogenetic Proteins (BMPs), Transforming Growth Factor betas (TGF-βs), including TGF-β-1, TGF-β-2, and TGF-β-3, Nell-1 protein, LIM mineralization protein and peptides; and combinations thereof.

The biologically active agent may be incorporated into the pore creating agent, and it may be released from the pore creating material as the pore creating agent is being removed and/or by diffusion. Alternatively, the biologically active agent may be encapsulated in or coated on the scaffolding material, and may be released as the scaffolding material is being resorbed or by diffusion. The biologically active agent is preferably administered over a period of between about 24 hours and about 12 weeks, and more preferably between about 24 hours and about 8 weeks, and most preferably between about 24 hours and about 6 weeks. Accordingly, whether the biologically active agent is incorporated into the pore creating agent, into the scaffolding material, or both depends on the desired administration period of the biologically active agent.

The instant compositions may be used to prepare therapeutic formulations. Such formulations may be prepared by mixing the instant compositions with optional physiologically acceptable carriers, excipients or stabilizers, in the form of lyophilized formulations or aqueous solutions. Methods for preparing therapeutic formulations are known and are disclosed, for example, in Remington: The Science and Practice of Pharmacy, $21^{st}$ edition, Lippincott Williams & Wilkins (2005).

By way of non-limiting example, following are some specific examples of instant compositions: Composition 1: scaffolding material comprises PVA hydrogel (25%-50% by volume), pore creating agent comprises liposome microspheres (100 micron diameter; 50-75% by volume; degrades within 72 hours), biologically active agent comprises TGF-Beta-1 (20 pg/mL to 3.0 ng/mL); delivered over 48 hours); Composition 2: scaffolding material comprises alginate (25%-50% by volume), pore creating agent comprises liposome microspheres (100 micron diameter; 50-75% by volume; degrades within 72 hours), biologically active agent comprises rhBMP-2 (100 ng/mL to 0.25 mg/mL, delivered over 72 hours); Composition 3: scaffolding material comprises epsilon caprolactone (25%-50% by volume); pore creating agent comprises liposome microspheres (100 micron diameter; 50-75% by volume; degrades within 72 hours), biologically active agent comprises TGF-Beta-1 (20 pg/mL to 3 ng/mL); delivered over 48 hours); and Composition 4: scaffolding material comprises PVA hydrogel (25%-50% by volume), pore creating agent comprises sodium bicarobonate microbubbles (100 micron diameter bubbles; 50-75% by volume; immediate removal upon injection of scaffold); biologically active agent comprises TGF-Beta-1 (20 pg/mL to 3 ng/mL; delivered over 48 hours).

In yet another aspect, a method for nucleus pulposus augmentation or replacement is provided. The method comprises administering to a patient a therapeutically effective amount of a composition, as described above. The term "therapeutically effective amount" means a quantity of an agent which, when administered to a patient or subject, is sufficient to result in an improvement in patient's condition. The improvement maybe determined in a variety of ways. Additionally, the improvement does not mean a cure and may include only a marginal change in patient's condition.

Initially, a surgeon would access the damaged disc to prepare the disc space to accept the instant compositions. Depending on the extent and the type of damage to nucleus pulposus, the nucleus pulposus tissue may be partially or fully removed. In some embodiments, however, the nucleus pulposus may be left fully in tact and only augmented using the instant compositions. Furthermore, if the annulus pulposus is ruptured, it may need to be closed to ensure that the composition is contained within the disc space during and after the delivery. Alternatively, a composition that is not likely to escape from disc space, such as a highly viscous or a rapidly setting composition, may be used when treating a disc with ruptured annulus pulposus.

Then, the instant compositions may be injected into the disc space. In embodiments where insufficient number of healthy nucleus pulposus cells are present in the disc space, the nucleus pulposus cells may also be administered in combination with the instant composition. The cells may be seeded into the instant composition or be administered separately. Although administering autologous nucleus pulposus cells is preferred, homologous cells or suitable stem cells may also be employed. Methods and techniques for isolating cells and seeding them on scaffolds are known and are disclosed in, for example, "Principles of Tissue Engineering," 3rd Edition, Academic Press (2007).

All publications cited in the specification, both patent publications and non-patent publications, are indicative of the level of skill of those skilled in the art to which this invention pertains. All of these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A composition for nucleus pulposus regeneration comprising an injectable scaffolding material and a pore creating agent dispersed within the scaffolding material, wherein the pore creating agent is removed from the scaffolding material in vivo to provide a porous scaffold for the regeneration of the nucleus pulposus.

2. The composition of claim 1, wherein the pore creating agent comprises microspheres.

3. The composition of claim 2, wherein the microspheres are made from hydrogel, fast resorbing cements, ceramics, hyaluronic acid, sugars, polysaccharides, chitin, or combinations thereof.

4. The composition of claim 1, wherein the pore creating agent comprises microbubbles.

5. The composition of claim 1, wherein the pore creating agent is removed over about 24 hours to about 48 hours.

6. The composition of claim 1, wherein the removal of the pore creating agent results in g a porosity of about 80 percent to about 95percent.

7. The composition of claim 1, wherein removal of the pore creating agent creates pores in the range of about 100 microns to about 200 microns.

8. The composition of claim 1, wherein the pore creating agent is loaded with at least one active agent.

9. The composition of claim 8, wherein the at least one active agent is selected from a group consisting of PDGF, IGF, TGF-Beta, BMPs and combinations thereof.

10. The composition of claim 8, wherein the active agent is released from the pore creating agent over about 24 hours to 42 days.

11. The composition of claim 7, wherein the pore creating agent is loaded with at least one active agent.

12. The composition of claim 11, wherein the at least one active agent is selected from a group consisting of PDGF, IGF, TGF-Beta, BMPs and combinations thereof.

13. The composition of claim 12, wherein the active agent is released from the pore creating agent over about 24 hours to about 42 days.

14. The composition of claim 1, further comprising nucleus pulposus cells.

15. A method of nucleus pulposus augmentation and replacement, the method comprising: administering to a patient a therapeutically effective about of a composition comprising a scaffolding material and a pore creating agent dispersed within the scaffolding material, wherein the pore creating agent is removed from the scaffolding material in vivo to provide a porous scaffold for the regeneration of the nucleus pulposus.

16. The method of claim 15, wherein the pore creating agent is loaded with at least one active agent.

17. The method of claim 16, wherein the at least one active agent is selected from a group consisting of PDGF, IGF, TGF-Beta, BMPs and combinations thereof.

18. The method of claim 16, wherein the biologically active agent is released over about 24 hours to 42 days.

19. The method of claim 15, wherein the removal of the pore creating agent creates pores in the range of about 100 microns to about 200 microns.

* * * * *